(12) United States Patent
Jorneus et al.

(10) Patent No.: US 7,491,058 B2
(45) Date of Patent: Feb. 17, 2009

(54) DENTAL IMPLANT SPACER AND ADAPTER ASSEMBLY

(75) Inventors: Lars Jorneus, Frillesas (SE); Anders Johansson, Göteborg (SE); Fredrik Kullberg, Lycke (SE)

(73) Assignee: Nobel Biocare Services AG, Glattbrugg (CH)

( * ) Notice: Subject to any disclaimer, the term of this patent is extended or adjusted under 35 U.S.C. 154(b) by 118 days.

(21) Appl. No.: 10/522,002

(22) PCT Filed: Jun. 4, 2003

(86) PCT No.: PCT/SE03/00899

§ 371 (c)(1),
(2), (4) Date: Oct. 21, 2005

(87) PCT Pub. No.: WO2004/002358

PCT Pub. Date: Jan. 8, 2004

(65) Prior Publication Data

US 2006/0110706 A1    May 25, 2006

(30) Foreign Application Priority Data

Jun. 27, 2002   (SE)   .................................... 0201996

(51) Int. Cl.
*A61C 8/00* (2006.01)
(52) U.S. Cl. ....................... 433/173; 433/172
(58) Field of Classification Search ................ 433/173, 433/172, 174, 175, 176, 169
See application file for complete search history.

(56) References Cited

U.S. PATENT DOCUMENTS 4,547,156 A * 10/1985 Hader ......................... 433/172
4,722,688 A    2/1988  Lonca
4,832,601 A    5/1989  Linden
4,850,870 A    7/1989  Lazzara et al.
4,854,872 A    8/1989  Detsch
4,904,187 A    2/1990  Zingheim
4,988,292 A    1/1991  Rosen
5,030,095 A    7/1991  Niznick
5,040,983 A    8/1991  Binon
5,106,300 A    4/1992  Voitik
5,135,395 A    8/1992  Marlin
5,152,687 A    10/1992 Amino (Continued)

FOREIGN PATENT DOCUMENTS

EP    0323421    7/1989

(Continued)

*Primary Examiner*—Melba Burngarner
(74) *Attorney, Agent, or Firm*—Knobbe Martens Olson & Bear LLP

(57) ABSTRACT

A spacer (3) with associated adapter (4) is designed to be fitted on an implant (1). The adapter comprises first and second portions (4b, 4c) designed to cooperate with the spacer and the implant, respectively, for securing the spacer on the implant. The adapter is completely enclosed by the spacer and the implant, and the first portion of the adapter can be designed with slits for forming resilient elements on said portion and/or with penetrating parts which, when the adapter and the spacer are joined together, are deformed as it penetrates into opposite parts in the spacer material. The spacer and the adapter can in this way be easily held together upon application to the implant and can be taken apart when completion work is performed on the spacer.

24 Claims, 2 Drawing Sheets

U.S. PATENT DOCUMENTS

| | | |
|---|---|---|
| 5,169,309 A | 12/1992 | Staubli et al. |
| 5,281,140 A | 1/1994 | Niznick |
| 5,328,371 A * | 7/1994 | Hund et al. ................. 433/173 |
| 5,344,457 A | 9/1994 | Pilliar et al. |
| 5,439,380 A | 8/1995 | Marlin |
| 5,480,304 A | 1/1996 | Nardi |
| 5,564,924 A | 10/1996 | Kwan |
| 5,733,124 A | 3/1998 | Kwan |
| 6,358,050 B1 | 3/2002 | Bergstrom et al. |
| 6,358,052 B1 | 3/2002 | Lustig et al. |
| 6,461,160 B1 * | 10/2002 | Sutter ......................... 433/173 |
| 6,743,018 B1 * | 6/2004 | Morrow ...................... 433/173 |
| 2003/0054319 A1 * | 3/2003 | Gerevais et al. ............. 433/173 |

FOREIGN PATENT DOCUMENTS

| | | |
|---|---|---|
| EP | 0419431 | 3/1991 |
| WO | WO 88/03391 | 5/1988 |
| WO | WO 85/02337 | 6/1995 |
| WO | WO 97/14372 | 4/1997 |
| WO | WO2000/0024335 | 4/2000 |

* cited by examiner

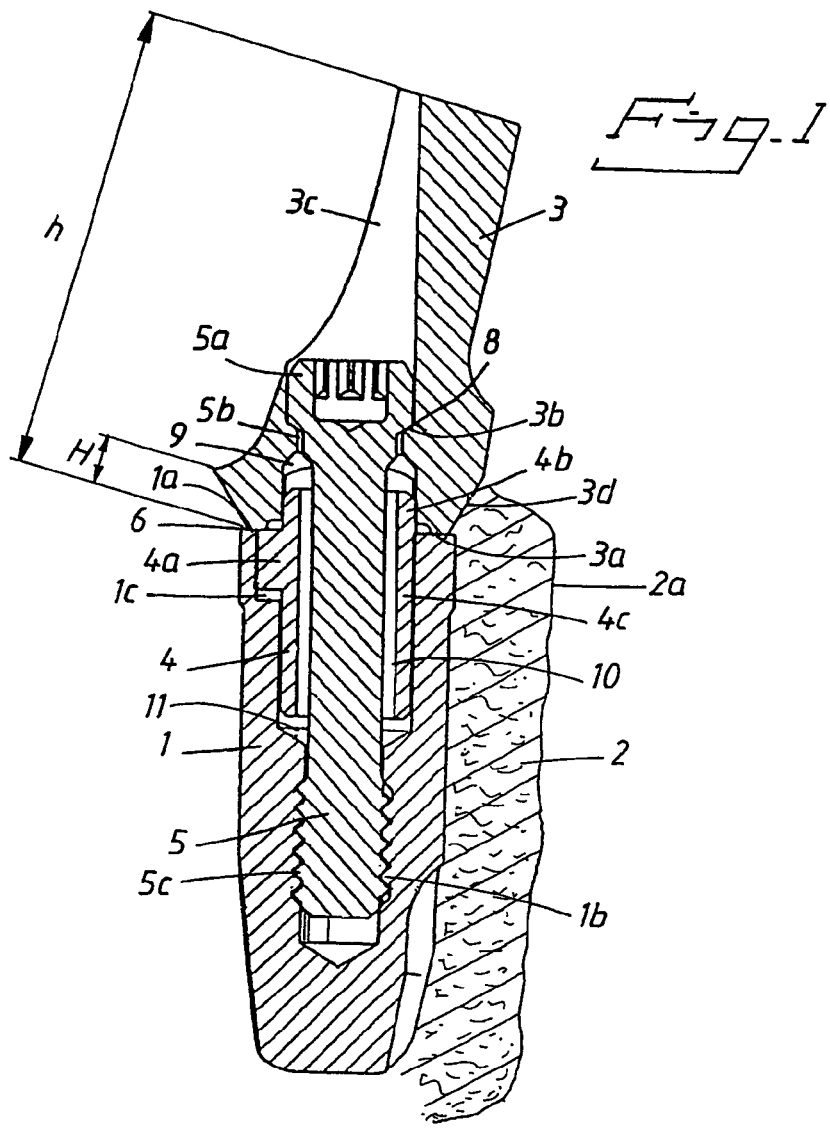
Fig. 1
Fig. 2
Fig. 3
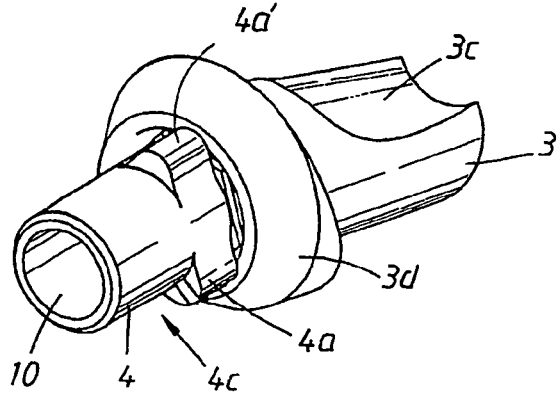
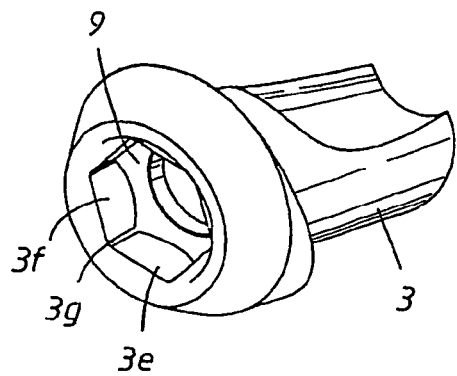

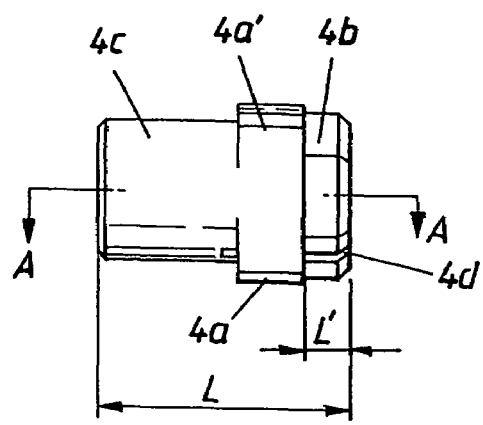
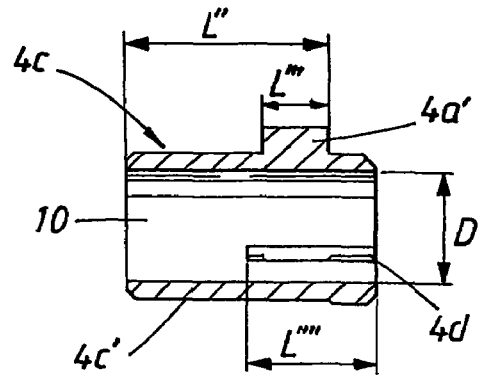
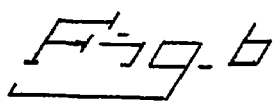
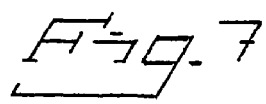
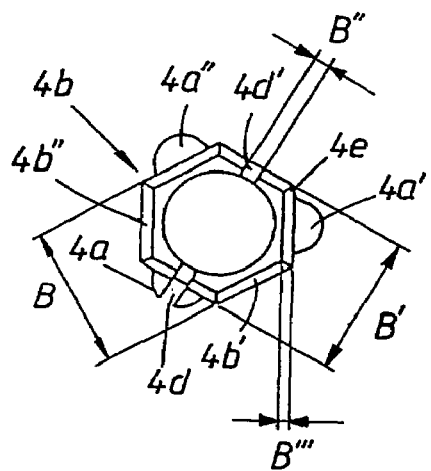
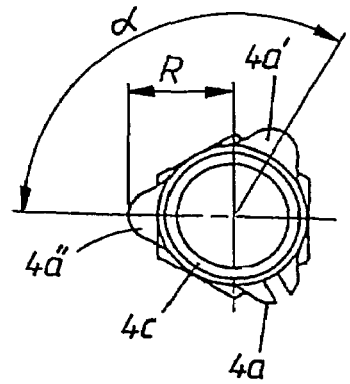

DENTAL IMPLANT SPACER AND ADAPTER ASSEMBLY

PRIORITY INFORMATION

This application is a U.S. National Phase of International Application No. PCT/SE2003/000899, filed Jun. 4, 2003, which claims the benefit of Swedish Patent Application No. 02 01996-6, filed Jun. 27, 2002.

The present invention relates to a spacer preferably made entirely of ceramic and with an associated adapter for securing the positions of the spacer in the lateral direction and the direction of rotation relative to an implant. The adapter can in this case comprise first and second portions designed to cooperate with the spacer and the implant, respectively, to achieve said securing of said positions.

In some situations it is desirable to couple what is referred to as a spacer to a dental implant. The spacer is usually made of metal, for example titanium or gold alloy. Spacers made of ceramics are also available and have great advantages compared to the metal spacers, for example it is possible to obtain more attractive colors with them, and porcelain can be burned directly onto the spacer. In this connection, reference is made, for example, to the known spacer called CerAdapt which is sold on the market by the Applicant of the present patent application. Said known spacer is a ceramic spacer intended to be joined to an implant with an external hexagon as connection geometry. The spacer is provided with a corresponding internal hexagon in its bottom geometry. Other types of implant can have an internal socket. The spacer is provided in these cases with a corresponding outwardly projecting geometry. These thin and tubular geometries can be difficult to produce using ceramics. This is because it is difficult to achieve correct filling of ceramic material in a mold cavity in which the ceramic powder is pressed down upon production. The tubular structures obtained are also too fragile for use in dental situations and it is additionally difficult to maintain the small or fine tolerances which are needed to ensure that the play between implant and spacer is minimal.

In accordance with the underlying concept of the invention, a metal component or metal adapter will be used in connection with the ceramic spacer. It has been proposed that the metal components known to date be shaped so that they fit into and fasten in the ceramic spacers. In this respect, reference may be made inter alia to EP 593926 B1, EP 867153 A1, and U.S. Pat. No. 6,343,930 B1. Said references illustrate problems which are associated with spacers and implants of the type in question.

In dental work with implants and spacers with associated adapters, there is a great need to be able to handle as few parts as possible. The invention proposes that the adapter will be able to be easily fitted onto the spacer and will obtain a fixed position in terms of lateral direction and direction of rotation relative to the spacer. There is also a need for the assembly to be able to be taken apart so that the spacer can be treated, for example said burning-on of porcelain, without the adapter being affected, for example discolored, and this guarantees a good implant result. Said burning requires high temperatures, for example, which means that the adapter may acquire a poor finish or even be deformed. In addition, thermal stresses could occur between the ceramic and metal components. The invention solves these problems, inter alia.

It is also important to have a wide choice regarding the configuration of the spacer. Thus, for example, the guide surface between the spacer and the implant must be able to be positioned high up, and the adjoining lower cone or equivalent on the spacer is given a low height. The arrangement must be able to be effectively protected against bacterial invasion, which entails a protected position for the whole adapter and the smallest possible number of gaps in the arrangement. The invention also solves these problems.

It is also important that, when it is fitted to the spacer and to the implant, the adapter is not exposed to strong forces, for example during chewing movements. It is also important that the chewing forces must be able to act on the arrangement in the longitudinal direction and contribute to the force anchoring the spacer with adapter to the implant. The invention also solves this problem.

That which can principally be regarded as characterizing a spacer with adapter according to the invention is that, when the spacer and the implant are joined together, the adapter is completely enclosed by the spacer and the implant. Further characteristics are that the first portion, mentioned at the outset, of the adapter is designed with one or more, preferably two, slits preferably extending in the longitudinal direction of the first portion and arranged to give the first portion resilient properties which effect or take part in the anchoring of the adapter to the spacer, and/or that the adapter is provided with penetrating parts which, when the adapter and the spacer are joined together, cause a deformation in the material contact surfaces.

In a preferred embodiment, the spacer, with the adapter applied to it, bears via a bottom surface against a top surface of the implant. The adapter enclosed inside the spacer and the implant is in contact with the outside of the arrangement only via a possible gap between the bottom and top surfaces, and the arrangement, for example the implant screw, for securing the spacer to the implant. Further characteristics of said embodiments can be attributed to the length of the first portion and to the fact that the guide surface in question between spacer and implant is positioned high up, i.e. near the top edge of the jaw bone. If slits are used, the first portion has a geometry which exceeds the geometry of a corresponding recess in the spacer when the spacer and the adapter are in the position in which they are not joined together. When the implant and the spacer are fitted together, the resilient parts in the first portion are pressed inwards and effect or take part in the securing function. Penetrating parts used as a complement to this or as an alternative can, in one embodiment, consist of corners of a polygon, for example a hexagon, which are deformed when they penetrate into blunt corners in a corresponding configuration in the spacer. The second portion can be provided with members which fix it in the direction of rotation and which in one embodiment can have a substantially semicircular shape. In the case with two or more such outwardly projecting members, these can be uniformly distributed about the circumference of the first portion.

Further embodiments of the inventive concept are set out in the attached dependent patent claims.

By means of what has been proposed above, an arrangement with spacer and adapter is obtained which is uncritical from the point of view of its function and permits considerable variations in the dental context. The surgeon, dentist or equivalent person can treat the spacer and its adapter as a single unit after the spacer and adapter have been joined together. The spacer and the adapter can easily be separated to permit separate treatment of the spacer.

An arrangement using the characteristics of the invention will be described below with reference to the attached drawings, in which:

FIG. 1 shows a vertical section through an implant to which a spacer with adapter has been fitted, FIG. 2 shows a perspective view, obliquely from underneath, of the spacer with fitted adapter, FIG. 3 shows a perspective view, obliquely from underneath, of the spacer without adapter, and FIGS. 4-7 show the design of the adapter in various views and sections.

In FIG. 1, an implant is indicated by reference number 1. The implant can be of a type known per se and will therefore not be discussed in detail here. The implant is anchored in a jaw bone which has been symbolized by 2, and this anchoring as such is also already known. A spacer which in the present case is made entirely of ceramic is fitted to the implant. Such spacers are also already known and, concerning their design and the types of material used, reference is made to the prior art. The spacer 3 is fitted to the implant with the aid of an adapter which in the present case is made of metal. The metal can be stainless steel, alloy, etc., of a type known per se. The spacer is anchored in the implant by means of an implant screw 5 with associated screw head 5a. The adapter 4 is fixed in the direction of rotation relative to the implant 1, and the spacer is fixed in the lateral direction and the direction of rotation relative to the adapter 4 in accordance with what is described below, which results in a rotationally rigid securing of the spacer to the implant 1. The implant has a top surface 1a and the spacer has a bottom surface 3a. The spacer and the implant bear against one another via said top and bottom surfaces. A gap which is present between said top and bottom surfaces is indicated by 6. The tightening with the implant screw 5 is here assumed to be such that the gap 6 has the value zero or only very low values. The screw head 5a has a bottom surface 5b which cooperates with an inner surface or inwardly projecting flange 3b. The tightening force for the screw is here assumed to be such that a suitable seal is obtained between screw head and spacer. A gap between the bottom surface 5b and the surface 3b of the spacer is indicated by 8, and this gap too is assumed to be 0 or to have only very low values. The screw extends through a recess 9 in the spacer 3, a recess 10 in the adapter 4, and a recess 11 in the implant. The screw has an external thread 5c which can cooperate with a corresponding internal thread 1b of the implant. For said lateral and rotational fixing between adapter and implant, the adapter has a number of outwardly projecting members 4a which can cooperate with corresponding recesses 1c in the implant. The lengths of the outwardly projecting members 4a are less than the lengths of the recesses 1c. The adapter can be regarded as consisting of two portions, here called a first portion 4b and a second portion 4c. In the first portion, the adapter extends into the recess 9 of the spacer and the second portion 4c extends into the recess 11 of the implant. The screw head 5a can be provided in a manner known per se with a wrench socket or screwdriver slot and the screw is fitted with its free end via a recess 3c in the spacer and is also screwed tight via this recess. By virtue of the arrangement shown, the adapter and the recesses in the spacer and the implant are exposed from the outside of the arrangement only via said gaps 6 and 8. A lower cone 3d is also shown on the spacer 3 in FIG. 1. The height of the cone can, in accordance with the arrangement, have a relatively low height H, which height in the present case can be, for example, a fifth of the total height h of the spacer. The guide surface 1a can in this way be given a high position and the broader part of the cone can be fitted near to the upper parts 2a of the jaw bone.

FIG. 2 shows the situation when the spacer 3 and the adapter 4 are in the joined-together position, i.e. the adapter's first portion (not shown in FIG. 2) is inserted into the spacer. The spacer and the adapter can in this way form a common unit which can be easily handled by the surgeon or equivalent person. FIG. 2 also shows two of said outwardly projecting members 4a, 4a'. In addition, the recesses 3c and 10 are also shown. The unit formed by the spacer and the adapter can be applied to an implant via said second portion 4c.

FIG. 3 shows the spacer with the adapter removed. The recess in the spacer intended for the first portion 4b (see FIG. 1) in this case consists of an internal hexagonal recess, of which two sides have been indicated by 3e and 3f. The side faces of the recess are connected by blunt corners, one of which has been indicated by 3g. The spacer in question is made of ceramic material and the adapter according to the above is made of metal or equivalent. In its first portion cooperating with the recess 9, the adapter has a hexagonal shape with sharp corners. When the first portion is fitted in the recess 9, the sharp corners of the hexagon are deformed by said rounded corners of the ceramic material, i.e. a material deformation in the contact surfaces means that a reliable and secure anchoring is achieved for the adapter in the spacer.

An illustrative embodiment of the structure of the adapter is shown in FIGS. 4-7. In FIG. 4, the total length of the adapter is indicated by L, which length can be ca. 4-5 mm. The length of the first portion 4b is indicated by L' and can be ⅓ to ⅕ of said total length. Said portion is provided with through-slits 4d which in the present case are two in number, but instead it is possible to provide one slit or a number of slits greater than two. In the present case the slits extend into the second portion 4c and through one of the outwardly projecting members, namely the member 4a. By means of the arrangement of slits, the first portion forms parts which operate with a resilient function.

According to FIG. 5, the second portion 4c has a length L" which together with the first portion 4b (see FIG. 4) forms the total length L of the adapter. The length of the outwardly projecting member 4a' has been designated as L'" and can, for example, have a value of ca. 1.1-1.4 mm. The length of the slit or slits 4d is indicated by L"", which can correspond to about half of the total length of the adapter. The recess 10 is substantially circular and has a diameter D which can have values of ca. 2 mm. At the parts 4c' of the second portion 4c, under the outwardly projecting members 4a', the adapter is substantially tubular.

According to FIG. 6, the hexagonal shape of the first portion 4b has breadths B, B' which can be identical or slightly different. In the present case, breadths of about 2.75 can be used. In the present case, two diametrically opposite slits 4d, 4d' are used. By means of the arrangement of slits, two resilient elements 4b' and 4b" are in principle obtained.

The breadths B and B' are chosen with greater diameters than the corresponding breadths of the hexagon shape in the recess 9 of the spacer. This means that, when the spacer and the adapter are joined together, the portions can spring inward and effect the retaining action in accordance with the above. In the position when not acted upon, the slits can have a breadth B" of ca. 0.3 mm. The wall thickness in the first portion of the adapter is indicated by B'" and can assume values of ca. 0.2 mm. All three outwardly projecting members 4a, 4a', 4a" are shown in FIG. 6. A sharp corner which, when the adapter is put together, has its material deformed in an opposite corner is indicated by 4e.

FIG. 7 also shows said outwardly projecting members 4, 4a', 4a", which members are uniformly distributed about the circumference, and the angle of separation between two outwardly projecting members 4a' and 4a" has been shown by α, which is ca. 120°. A value R has also been indicated between the longitudinal axis of the adapter and the outermost part of the outwardly projecting member 4a". This value can be ca. 1.8 mm.

The height H can be ⅓ to ⅕ of the height h. The first portion can have a length which is ⅓ to ⅕ of the length L. The spacer and the adapter can be released from the joined-together position and can then be joined together again or joined to another spacer or adapter, respectively, with a corresponding assembly function.

The invention is not limited to the embodiment shown above by way of example and instead it can be modified within the scope of the attached patent claims and the inventive concept.

The invention claimed is:

1. A dental assembly, comprising: a ceramic spacer and an adapter for securing the spacer in a lateral direction and a rotational direction relative to an implant, said adapter comprising a first portion configured to cooperate with the spacer and a second portion configured to cooperate with the implant to secure the spacer relative to the implant, the first portion defining a geometry which exceeds a geometry of a corresponding recess in the spacer when the first portion is not inserted into the recess of the spacer, the first portion comprising parts that are moved resiliently inwardly when the first portion is inserted into the recess of the spacer, wherein the adapter is completely enclosed by the spacer and the implant when the spacer is fitted on the implant, and wherein the first portion of the adapter additionally comprises at least one slit configured to give the first portion resilient properties to secure the adapter to the spacer, and wherein the second portion comprises outwardly projecting members configured to generally restrict rotation of the second portion relative to the implant.

2. The dental assembly as in claim 1, wherein the spacer, with the adapter applied to it, bears via a bottom surface against a top surface of the implant, and wherein the adapter enclosed in the spacer and the implant is exposed to outsides of the spacer and of the implant only via a gap located between the bottom and top surfaces of the spacer and implant, and wherein the assembly comprises a locking screw for securing the spacer to the implant.

3. The dental assembly as in claim 1 wherein the first portion has a length of about ⅓ to about ⅕ of the total length of the adapter, and wherein the spacer has a cone shaped portion with an outer surface facing the implant and which has a height which is about ⅓ to ⅕ of the total height of the spacer.

4. The dental assembly as in claim 1, wherein said at least one slit extends along the whole extent of the first portion and into parts of the second portion.

5. The dental assembly as in claim 1, wherein said at least one slit extends along about half of the total length of the adapter.

6. The dental assembly as in claim 1, wherein the first portion has a polygonal external cross section.

7. The dental assembly as in claim 1, wherein in cross section, the outwardly projecting members comprise substantially semicircular members which can be placed opposite corresponding recesses in the implant.

8. The dental assembly as in claim 7, wherein the second portion comprises three outwardly projecting members that are uniformly distributed about the circumference.

9. The dental assembly as in claim 8, wherein the at least one slit extends through at least one of said projecting members.

10. The dental assembly as in claim 1, wherein the spacer and the adapter are removably attachable to one another.

11. The dental assembly as in claim 1, wherein when the spacer is in its position fitted on the implant, the adapter takes up a position which is substantially unaffected in the longitudinal direction of the adapter.

12. The dental assembly as in claim 1, wherein when the adapter is in a position enclosed by the spacer and by the implant, the adapter cannot be acted upon in the longitudinal direction of the adapter and cannot be acted upon by lateral forces or bending forces.

13. The dental assembly as in claim 1, wherein the adaptor includes penetrating parts that are configured such that when the adapter and the spacer are joined together, a deformation occurs in material contact surfaces between the adaptor and the spacer.

14. The dental assembly as in claim 1, wherein the adapter includes a plurality of slits.

15. The dental assembly as in claim 1, wherein the at least one slit extends in a longitudinal direction with respect to the adapter.

16. A dental assembly comprising a ceramic spacer and an adapter for securing the spacer in a lateral direction and a rotational direction relative to an implant, said adapter comprising a first portion and a second portion configured to cooperate with the spacer and the implant, respectively, to secure the spacer relative to the implant wherein the adapter is completely enclosed by the spacer and the implant when the spacer is fitted on the implant, the first portion of the adapter comprising penetrating parts, the penetrating parts comprising corners of a polygon configured to deform against contact surfaces of the spacer when the adapter and the spacer are joined together, wherein the second portion comprises outwardly projecting members configured to generally restrict rotation of the second portion relative to the implant.

17. The dental assembly as in claim 16, wherein the contact surfaces of the spacer comprise interior corners of a recess of the spacer.

18. The dental assembly as in claim 16, wherein the penetrating parts comprise projecting parts which are deformed against an opposite surface in the spacer.

19. A dental assembly, comprising: a ceramic spacer and an adapter for securing the spacer in a lateral direction and a rotational direction relative to an implant, said adapter comprising a first portion configured to cooperate with the spacer and a second portion figured to cooperate with the implant to secure the spacer relative to the implant, wherein the adapter is completely enclosed by the spacer and the implant when the spacer is fitted on the implant and wherein the second portion comprises outwardly projecting members configured to restrict rotation of the second portion relative to the implant and the first portion of the adapter comprises at least one slit configured to give the first portion resilient properties to secure the adapter to the spacer.

20. The dental assembly as in claim 19, wherein said at least one slit extends along the whole extent of the first portion and into parts of the second portion.

21. The dental assembly as in claim 19, wherein said at least one slit extends along about half of the total length of the adapter.

22. The dental assembly as in claim 19, wherein in cross section, the outwardly projecting members comprise substantially semicircular members which can be placed opposite corresponding recesses in the implant.

23. The dental assembly as in claim 19, wherein the second portion comprises three outwardly projecting members that are uniformly distributed about the circumference of the second portion.

24. The dental assembly as in claim 19, wherein the at least one slit extends through at least one of said projecting members.

* * * * *

UNITED STATES PATENT AND TRADEMARK OFFICE
CERTIFICATE OF CORRECTION

PATENT NO. : 7,491,058 B2
APPLICATION NO. : 10/522002
DATED : February 17, 2009
INVENTOR(S) : Jorneus et al.

Page 1 of 1

It is certified that error appears in the above-identified patent and that said Letters Patent is hereby corrected as shown below:

In Column 6, line 40, in Claim 19, please change "figured" to -- configured --.

Signed and Sealed this

Twenty-third Day of June, 2009

JOHN DOLL
*Acting Director of the United States Patent and Trademark Office*